United States Patent
Ongini et al.

(10) Patent No.: US 9,895,335 B2
(45) Date of Patent: Feb. 20, 2018

(54) OPHTHALMIC COMPOSITIONS CONTAINING A NITRIC OXIDE DONOR

(71) Applicant: NICOX SCIENCE IRELAND, Dublin (IE)

(72) Inventors: Ennio Ongini, Segrate (IT); Nicoletta Almirante, Milan (IT); Laura Storoni, Cesano Maderno (IT); Elena Bastia, Milan (IT)

(73) Assignee: NICOX SCIENCE IRELAND, Dublin (IE)

( * ) Notice: Subject to any disclaimer, the term of this patent is extended or adjusted under 35 U.S.C. 154(b) by 0 days.

(21) Appl. No.: 14/904,747

(22) PCT Filed: Jul. 7, 2014

(86) PCT No.: PCT/EP2014/064401
§ 371 (c)(1),
(2) Date: Jan. 13, 2016

(87) PCT Pub. No.: WO2015/007552
PCT Pub. Date: Jan. 22, 2015

(65) Prior Publication Data
US 2016/0158182 A1   Jun. 9, 2016

(30) Foreign Application Priority Data
Jul. 15, 2013   (EP) .................... 13176521

(51) Int. Cl.
A01N 57/00    (2006.01)
A61K 31/66    (2006.01)
A61K 31/22    (2006.01)
A61K 45/06    (2006.01)
A61K 9/00     (2006.01)
C07C 203/04   (2006.01)
A61K 31/215   (2006.01)

(52) U.S. Cl.
CPC ............ *A61K 31/22* (2013.01); *A61K 9/0048* (2013.01); *A61K 31/215* (2013.01); *A61K 45/06* (2013.01); *C07C 203/04* (2013.01)

(58) Field of Classification Search
None
See application file for complete search history.

(56) References Cited

U.S. PATENT DOCUMENTS

| | | | |
|---|---|---|---|
| 2002/0168424 A1 | 11/2002 | Shahinpoor et al. | |
| 2009/0062296 A1 | 3/2009 | Benedini et al. | |
| 2010/0099729 A1* | 4/2010 | Almirante | C07C 229/08 514/412 |
| 2011/0300097 A1* | 12/2011 | Al-Qahtani | A61K 9/0048 424/85.2 |

FOREIGN PATENT DOCUMENTS

| | | |
|---|---|---|
| EP | 1 481 668 A1 | 12/2004 |
| WO | WO 2009/000723 A1 | 12/2008 |
| WO | WO2011041870 A1 * | 4/2011 |

OTHER PUBLICATIONS

STN registry database compound 1100273-14-0 (entered STN Feb. 3, 2009).*
Ito et al. (Cancer Science, 94 (1), 3-8, 2003).*
International Search Report of PCT/EP2014/064401 dated Aug. 19, 2014.

* cited by examiner

*Primary Examiner* — Dennis Heyer
*Assistant Examiner* — Daniel M Podgorski
(74) *Attorney, Agent, or Firm* — Arent Fox LLP

(57) ABSTRACT

The present invention relates to compositions comprising a 4-nitrooxybutan-1-ol alkyl ester as nitric oxide donor. More specifically, the invention relates to compositions comprising 4-nitrooxybutan-1-ol alkyl ester as a nitric oxide donor and an ophthalmic drug, useful in controlling elevated intraocular pressure associated with glaucoma or ocular hypertension associated with other diseases or conditions. The invention is also directed to methods of controlling intraocular pressure utilizing said compositions.

20 Claims, No Drawings

OPHTHALMIC COMPOSITIONS CONTAINING A NITRIC OXIDE DONOR

CROSS-REFERENCE TO RELATED APPLICATION

This application is a National Stage entry of International Application No. PCT/EP2014/064401, filed Jul. 7, 2014, which claims priority to European Patent Application No. 13176521.6, filed Jul. 15, 2013. The disclosures of the prior applications are hereby incorporated in their entirety by reference.

The present invention relates to compositions comprising a 4-nitrooxybutan-1-ol alkyl ester as nitric oxide donor. More specifically, the invention relates to compositions comprising 4-nitrooxybutan-1-ol alkyl ester as a nitric oxide donor and an ophthalmic drug, useful in controlling elevated intraocular pressure associated with glaucoma or ocular hypertension associated with other diseases or conditions. The invention is also directed to methods of controlling intraocular pressure utilizing said compositions.

Numerous disorders of the eye lead to an increase in intraocular pressure (TOP). For example, glaucoma, post-surgical or post-laser trabeculectomy, ocular hypertensive episodes, trauma, ischemia and steroidal anti-inflammatory drugs therapy all can result in increased IOP.

Glaucoma, including normotensive and hypertensive glaucoma, is a disease of the eye characterized by a progressive loss of visual field due to irreversible damage to the optic nerve to the point where, if untreated, may result in total blindness. Hypertensive glaucoma occurs when an imbalance in production and drainage of fluid in the eye (aqueous humor) increases eye pressure to unhealthy levels.

Conversely, normotensive glaucoma occurs despite the intraocular pressure is kept to reasonably low levels.

The loss of visual field, in one form of primary open angle glaucoma (POAG), is associated with a sustained increase in the intraocular pressure of the diseased eye. Moreover, elevated intraocular pressure without visual field loss is thought to be indicative of the early stages of this form of POAG.

Normotensive glaucoma is a chronic progressive optic neuropathy resulting in typical optic nerve head changes, retinal nerve fibers layer defects, and characteristic visual field defects. In addition, the chamber angle is open and IOP values within statistical normal limits (lower than 22 mmHg) (Lee et al. 1998; for review, see Hoyng and Kitazawa 2002).

There is evidence that treatment of normotensive glaucoma by lowering TOP can slow the glaucomatous process. A reduction of at least 30% in TOP is needed to induce a favorable improvement in this disease.

Secondary Open Angle Glaucoma can be caused by any variety of substances that mechanically block the outflow of aqueous humor through the trabecular meshwork, resulting in elevated TOP. These substances include pigment, exfoliation material and red blood cells.

Other pathologies can lead to an elevation of TOP, steroidal anti-inflammatory drugs currently used for treating diseases of the macula, such as age-related macular degeneration and diabetic macular edema, and in the treatment of ocular inflammation are associated with elevation of intraocular pressure.

Elevated intraocular pressure is also a common post-surgical complication following ocular surgery such as pars plana vitrectomy, vitreoretinal surgery, retinal detachment surgery, panretinal photocoagulation.

Prior art treatment of glaucoma consists in lowering the intraocular pressure by administering drugs which either reduce the production of aqueous humor within the eye or increase the fluid drainage, such as beta-blockers, α-agonists, cholinergic agents, carbonic anhydrase inhibitors, prostaglandin analogs. However several side effects are associated with the drugs conventionally used to treat glaucoma.

Beta-blockers show serious pulmonary side effects, depression, fatigue, confusion, impotence, hair loss, heart failure and bradycardia.

α-Agonists have a fairly high incidence of allergic or toxic reactions.

Cholinergic agents (miotics) can cause visual side effects.

The side effects associated with carbonic anhydrase inhibitors include fatigue, anorexia, depression, paresthesias and serum electrolyte abnormalities (The Merck Manual of Diagnosis and Therapy, Seventeenth Edition, M. H. Beers and R. Berkow Editors, Sec. 8, Ch. 100).

Finally, prostaglandin analogs (bimatoprost, latanoprost, travoprost, tafluprost and unoprostone isopropyl) used in the treatment of glaucoma can produce ocular side effects, such as increased pigmentation of the iris, ocular irritation, conjunctival hyperaemia, iritis, uveitis and macular oedema (Martindale, Thirty-third edition, p. 1445).

It is known that in the eye, nitric oxide (NO) has an important role in certain physiological processes, e.g. regulation of aqueous humor dynamics, vascular tone, retinal neurotransmission, phototransduction and ocular immunological responses. Conversely, the excess formation of NO is involved in degeneration processes in the eye.

U.S. Pat. No. 4,590,207 discloses ophthalmic solution containing isosorbide mononitrate as an active ingredient for treating and/or preventing intraocular hypertension and glaucoma.

US patent application 2002/0168424 discloses the use of a mixture of a nitric oxide (NO) donor such as nitrovasodilators like minoxidil, nitroglycerin, L-arginine, isosorbide dinitrate, or nitroprusside, and a cyclic guanosine 3',5'-monophosphate (cGMP) specific phosphodiesterase type 5 (PDE5) inhibitor such as sildenafil citrate for treating glaucoma or ocular hypertension. The disclosed combinations promote systemic vascular relaxation, enhance blood flow to the optic nerve, dilation of the trabecular meshwork, the Schlemm's canal and uveoscleral outflow channel tissues, enhance aqueous humor drainage and thus lowered intraocular pressure (TOP) in mammalian eye.

Organic nitrates have been used for over a century in the treatment of cardiac diseases however, it is known that the classical organic nitrates used in therapy, such as glycerol trinitrate, isosorbide dinitrate or isosorbide 5-mononitrate, undergo tolerance and lose their activity upon repeated administration. Nitrate tolerance develops despite an elevation in the drug plasma concentration reflecting a decrease in vascular sensitivity to previously therapeutic levels. It is also reported that in animal models, nitroglycerin showed diminished ocular response after chronic administration. J Pharmacol Exp. Ther. 1992; 260:956-65.

WO2009/000723 discloses 4-nitrooxybutan-1-ol alkyl ester as intermediates of the industrial preparation of 4-nitrooxybutan-1-ol that is a key intermediate for the synthesis of a known NO-releasing derivative of naproxen that is 2-(S)-(6-methoxy-2-naphtyl)-propanoic acid 4-nitrooxybutyl ester.

Although the prior art has provided information about the potential therapeutic effects of NO and/or some NO donor compounds, it also suggests that excess NO production can have untoward effects on ocular tissues.

Based on the prior art, it is difficult to provide nitric oxide donor compounds useful for ophthalmic compositions.

Therefore, the technical problem underlying the present invention is to provide effective ophthalmic compositions for treating and/or preventing ocular hypertension having reduced side effects and enhanced patient compliance.

The present invention provides nitric oxide donors 4-nitrooxybutan-1-ol alkyl ester for use to lower intraocular pressure and suitable for use as part of ophthalmic compositions. In particular, topical application of ophthalmic compositions comprising these nitric oxide donors 4-nitrooxybutan-1-ol alkyl esters result in significant TOP reduction. Since nitric oxide donors 4-nitrooxybutan-1-ol alkyl esters have an activity of lowering ocular pressure al low doses, the combination of these 4-nitrooxybutan-1-ol alkyl esters and known ophthalmic drugs can be used for the treatment of various disease and conditions in which lowering of ocular pressure is desired, for example glaucoma, ocular hypertension and other conditions which accompanies increase in ocular pressure.

The ophthalmic composition including a nitric oxide donor 4-nitrooxybutan-1-ol alkyl ester and an ophthalmic drug has an advantage, that it has a synergistically increased ocular hypotensive action, thus the ophthalmic drug may be used at a reduced concentration decreasing or eliminating troublesome side effects while the combined effect on reducing intraocular pressure remains in the therapeutically useful range.

The use of these combinations has the further advantage of reducing intraocular pressure via two different mechanisms.

The present invention relates to compositions comprising
(A) a nitric oxide donor of the following formula (I) or a stereoisomer thereof:

RC(O)O—(CH$_2$)$_4$—ONO$_2$  (I)

wherein R is a linear or branched (C$_3$-C$_5$)-alkyl chain, and
(B) an ophthalmic drug selected from one of the following groups: alpha adrenergic agonists, beta blockers, carbonic anhydrase inhibitors, prostaglandin analogs, cholinergic agonists, non-steroidal anti-inflammatory and steroidal anti-inflammatory drugs.

Linear or branched (C$_3$-C$_5$)-alkyl chain may be for example propyl, iso-propyl, butyl, sec-butyl, tert-butyl, preferably butyl.

A preferred embodiment of the invention provides compositions comprising:
(A) a nitric oxide donor of formula (I) that is

CH$_3$(CH$_2$)$_2$C(O)O—(CH$_2$)$_4$—ONO$_2$  (Ia)

and
(B) an ophthalmic drug selected from one of the following groups: alpha adrenergic agonists, beta blockers, carbonic anhydrase inhibitors, prostaglandin analogues, cholinergic agonists, non-steroidal anti-inflammatory drugs and steroidal anti-inflammatory drugs.

Another embodiment of the invention provides compositions comprising:
(A) a nitric oxide donor of formula (I) as defined above or stereoisomers thereof; and
(B) a carbonic anhydrase inhibitor selected from dorzolamide, brinzolamide.

Another embodiment of the invention provides compositions comprising:
(A) a nitric oxide donor of formula (I) as defined above or stereoisomers thereof; and (B) a beta blocker selected from timolol, carteolol, betaxolol, levobunolol or metipranolol, preferably timolol or levobunolol.

Another embodiment of the invention provides compositions comprising:
(A) a nitric oxide donor of formula (I) as defined above or stereoisomers thereof; and
(B) an alpha-adrenergic agonists selected from brimonidine, apraclonidine, epinephrine or dipivefrin, preferably brimonidine or apraclonidine.

Another embodiment of the invention provides compositions comprising:
(A) a nitric oxide donor of formula (I) as defined above or stereoisomers thereof; and
(B) a prostaglandin analogue selected from bimatoprost, latanoprost, travoprost, unoprostone isopropyl and tafluprost.

Another embodiment of the invention provides compositions comprising:
(A) a nitric oxide donor of formula (I) as defined above or stereoisomers thereof, and
(B) a cholinergic agonist selected from pilocarpin, carbacol and echothiophate.

Another embodiment of the invention provides compositions comprising:
(A) a nitric oxide donor of formula (I) as defined above or stereoisomers thereof, and
(B) a non-steroidal anti-inflammatory drug selected from bromfenac, flurbiprofen, naproxen and ketoprofen.

Another embodiment of the invention provides compositions comprising:
(A) a nitric oxide donor of formula (I) as defined above or stereoisomers thereof and
(B) a steroidal anti-inflammatory drug selected from dexamethasone, fluocinolone acetonide, triamcinolone acetonide, budesonide and prednisolone.

Another preferred embodiment of the invention provides compositions comprising:
(A) a nitric oxide donor of formula (Ia) as defined above; and
(B) a carbonic anhydrase inhibitor selected from dorzolamide, brinzolamide.

Another preferred embodiment of the invention provides compositions comprising:
(A) a nitric oxide donor of formula (Ia) as defined above; and
(B) a beta blocker selected from timolol, carteolol, betaxolol, levobunolol or metipranolol, preferably timolol or levobunolol.

Another preferred embodiment of the invention provides compositions comprising:
(A) a nitric oxide donor of formula (Ia) as defined above; and
(B) an alpha-adrenergic agonist selected from brimonidine, apraclonidine, epinephrine or dipivefrin, preferably brimonidine or apraclonidine.

Another preferred embodiment of the invention provides compositions comprising:
(A) a nitric oxide donor of formula (Ia) as defined above; and
(B) a prostaglandin analogue selected from bimatoprost, latanoprost, travoprost, unoprostone isopropyl or tafluprost.

Another preferred embodiment of the invention provides compositions comprising:
(A) a nitric oxide donor of formula (Ia) as defined above; and (B) a cholinergic agonist selected from pilocarpine, carbacol or echotiophate.

Another preferred embodiment of the invention provides compositions comprising:

(A) a nitric oxide donor of formula (Ia) as defined above; and (B) a non-steroidal anti-inflammatory drug selected from bromfenac, flurbiprofen, naproxen and ketoprofen.

Another preferred embodiment of the invention provides compositions comprising:

(A) a nitric oxide donor of formula (Ia) as defined above; and (B) a steroidal anti-inflammatory drug selected from dexamethasone, fluocinolone acetonide, triamcinolone acetonide, budesonide and prednisolone.

A most preferred embodiment of the invention provides compositions comprising:

(A) a nitric oxide donor of formula (Ia) as defined above; and (B) an ophthalmic drug selected from bimatoprost, latanoprost, travoprost, tafluprost, unoprostone isopropyl, apraclonidine, bromonidine, timolol, levobunolol, dorzolamide or brinzolamide.

Another embodiment of the invention provides the use of compositions comprising (A) a nitric oxide donor of formula (I) as defined above or stereoisomers thereof; and (B) an ophthalmic drug selected from one of the following groups: alpha adrenergic agonists, beta blockers, carbonic anhydrase inhibitors, prostaglandin analogs, cholinergic agonist, non-steroidal anti-inflammatory or steroidal anti-inflammatory drugs, for controlling elevated intraocular pressure associated with glaucoma and ocular hypertension associated with other diseases or conditions.

Another embodiment of the invention provides the use of compositions comprising:

(A) a nitric oxide donor of formula (I) as defined above or stereoisomers thereof; and (B) an ophthalmic drug selected from one of the following groups: alpha adrenergic agonists, beta blockers, carbonic anhydrase inhibitors, prostaglandin analogs, cholinergic agonist, non-steroidal anti-inflammatory or steroidal anti-inflammatory drugs for the treatment and/or prophylaxis of hypertensive glaucoma, normotensive glaucoma, secondary glaucoma, neovascular glaucoma and ocular hypertension.

Another embodiment of the invention provides the use of compositions comprising:

(A) a nitric oxide donor of formula (I) as defined above or stereoisomers thereof; and (B) an ophthalmic drug selected from one of the following groups: alpha adrenergic agonists, beta blockers, carbonic anhydrase inhibitors, prostaglandin analogs, cholinergic agonist, non-steroidal anti-inflammatory or steroidal anti-inflammatory drugs for the treatment of high intraocular pressure resulting from orbital edema, ischemia, trauma insults, post-surgical complications, intraocular inflammation, pupillary block or idiopathic causes.

Another embodiment of the invention provides the use of compositions comprising (A) a nitric oxide donor of formula (I) as defined above or stereoisomers thereof; and (B) an ophthalmic drug selected from non-steroidal anti-inflammatory or steroidal anti-inflammatory drugs for the treatment or prophylaxis of age related macular degeneration, diabetic retinopathy, retinal vein occlusion, macular degeneration, inflammatory retinal disease and uveitis.

Another preferred embodiment of the invention provides the use of the compositions comprising:

(A) a nitric oxide donor of formula (Ia) as defined above or stereoisomers thereof; and (B) an ophthalmic drug selected from one of the following groups: alpha adrenergic agonists, beta blockers, carbonic anhydrase inhibitors, prostaglandin analogues, cholinergic agonist, non-steroidal anti-inflammatory drugs and steroidal anti-inflammatory drugs, for controlling elevated intraocular pressure associated with glaucoma and ocular hypertension associated with other diseases or conditions.

Another preferred embodiment of the invention provides the use of the compositions comprising:

(A) a nitric oxide donor of formula (Ia) as defined above; and (B) an ophthalmic drug selected from one of the following groups: alpha adrenergic agonists, beta blockers, carbonic anhydrase inhibitors, prostaglandin analogues, cholinergic agonist, non-steroidal anti-inflammatory drugs or steroidal anti-inflammatory drugs, for the treatment and/or prophylaxis of hypertensive glaucoma, normotensive glaucoma, secondary glaucoma, neovascular glaucoma and ocular hypertension.

Another preferred embodiment of the invention provides the use of the compositions comprising:

(A) a nitric oxide donor of formula (Ia) as defined above; and (B) an ophthalmic drug selected from one of the following groups: alpha adrenergic agonists, beta blockers, carbonic anhydrase inhibitors, prostaglandin analogues, cholinergic agonist, non-steroidal anti-inflammatory drugs and steroidal anti-inflammatory drugs, for the treatment of high intraocular pressure resulting from orbital edema, ischemia, trauma insults, post-surgical complications, intraocular inflammation, pupillary block or idiopathic causes.

Another preferred embodiment of the invention provides the use of the compositions comprising:

(A) a nitric oxide donor of formula (Ia) as defined above; and (B) an ophthalmic drug selected from non-steroidal anti-inflammatory drugs or steroidal anti-inflammatory drugs, for the treatment or prophylaxis of age related macular degeneration, diabetic retinopathy, retinal vein occlusion, macular degeneration, inflammatory retinal disease and uveitis.

Another embodiment of the invention provides the use of a nitric oxide donor of formula (I) as defined above or stereoisomers thereof for controlling elevated intraocular pressure associated with glaucoma and ocular hypertension associated with other diseases or conditions.

Another preferred embodiment of the invention provides the use of a nitric oxide donor of formula (Ia) as defined above for controlling elevated intraocular pressure associated with glaucoma and ocular hypertension associated with other diseases or conditions.

Another preferred embodiment of the invention provides the use of a nitric oxide donor of formula (Ia) as defined above for the treatment of hypertensive glaucoma, normotensive glaucoma, secondary glaucoma, neovascular glaucoma and ocular hypertension.

Another preferred embodiment of the invention provides the use of a nitric oxide donor of formula (Ia) as defined above for the treatment or prophylaxis of age related macular degeneration, diabetic retinopathy, retinal vein occlusion, macular degeneration, inflammatory retinal disease and uveitis.

Another preferred embodiment of the invention provides the use of a nitric oxide donor of formula (Ia) as defined above for the treatment of high intraocular pressure resulting from orbital edema, ischemia, trauma insults, post-surgical complications, intraocular inflammation, pupillary block or idiopathic causes.

Another embodiment of the present invention provides pharmaceutical formulation for topical, periocular or intraocular administration comprising at least a nitric oxide donor of formula (I) and at least an ophthalmically acceptable excipient and/or ophthalmically acceptable vehicle.

Another embodiment of the present invention provides pharmaceutical formulation for topical, periocular or intraocular administration comprising the nitric oxide donor of formula (Ia) as defined above and at least an ophthalmically acceptable excipient and/or ophthalmically acceptable vehicle.

Another embodiment of the present invention provides pharmaceutical formulation for topical, periocular or intraocular administration comprising the compositions of the invention and at least an ophthalmically acceptable component and/or ophthalmically acceptable vehicle.

The preferred route of administration of the compositions of the invention is topical or intravitreal. The compounds and compositions of the present invention can be administered as solutions, suspensions, emulsions, or dispersions for topical use or as topical eye drops, gel tears.

The compositions for use in the current invention can also be administered via periocular administration, and may be formulated in solutions or suspensions for periocular administration. Formulations useful for periocular administration will generally be periocular injection formulations or surgical irrigating solutions. Periocular administration refers to administration to tissues near the eye, such as administration to the tissues or spaces surrounding the eyeball and within the orbit. Periocular administration can take place by injection, deposit, or any other mode of placement.

The compounds and the compositions of the present invention compositions may be formulated in solutions or suspensions for intraocular administration. Compositions useful for intraocular administration will generally be intraocular injection compositions or surgical irrigating solutions.

An "ophthalmically acceptable" component refers to a component which will not cause any significant ocular damage or ocular discomfort at the intended concentration and over the time of intended use. Solubilizers and stabilizers should be non-reactive. An "ophthalmically acceptable vehicle" refers to any substance or combination of substances which are non-reactive with the compounds and suitable for administration to a patient.

The nitric oxide donors of the present invention will generally be contained in the topical, periocular, or intraocular compositions and pharmaceutical formulations contemplated herein in an amount of from about 0.001 to about 10.0% weight/volume. Preferred concentrations will range from about 0.01 to about 5.0% w/v.

The ophthalmic drug will generally be contained in the topical, periocular, or intraocular compositions and pharmaceutical formulations contemplated herein in an amount of from about 0.001 to about 10.0% weight/volume. Preferred concentrations will range from about 0.01 to about 5.0% w/v.

General Synthesis

The NO donors of formula (I) can be prepared by step a) reacting an excess of 1,4-butanediol with an acid of formula R—C(O)OH wherein R is a linear or branched $(C_3-C_5)$-alkyl chain, preferably R is a linear $C_3$ alkyl chain, in the presence of an acidic catalyst and in an aliphatic apolar solvent, followed by selective separation of 1,4-butanediol monoester of formula (I)

wherein R is as above defined, from reaction mixture;

step b) nitration of 1,4-butanediol monoester with a mixture of conc. $H_2SO_4$ and conc. $HNO_3$, or a mixture of nitric acid and acetic acid or acetic anhydride, followed by isolation of the 4-nitrooxybutan-1-ol monoester of formula (II),

wherein R is as above defined;

EXAMPLE 1

Preparation of 4-Nitrooxybutan-1-Ol Butyrate (Compound (Ia))

Step a) Preparation of 1,4-Butanediol Monobutyrate

Toluenesulfonic acid monohydrate (2.12 g, 11.1 mmol), butyric acid (368 mL, 4.00 mol) 1,4-butanediol (1067 mL, 12.00 mol) and n-octane (750 mL) were mixed in a 2.5 L reaction vessel and the resulting emulsion was stirred vigorously at reflux for 1 h during which the water formed was removed by azeotropic distillation of the n-octane-water azeotrope. The mixture was allowed to cool to room temperature and the octane-layer was separated from the butanediol-layer containing the product and the latter phase was extracted four times with petrol ether 80/110 (300 mL for each extraction). The so obtained butanediol-layer was extracted three times with dichloromethane (500 mL for each extraction) and after phase separation the dichloromethane-layers were combined and washed four times with water (200 mL for each extraction). Removal of the dichloromethane by distillation and drying of the residue using a jacket temperature of 70° C. gave 499 g (78%) of the title compound having a chromatographic purity of 99.1% (gas chromatography) and a water content of 0.27%. This was used without further treatment in the synthesis of 4-nitrooxybutan-1-ol butyrate.

Step b) Preparation of 4-Nitrooxybutan-1-Ol Butyrate (Compound (Ia))

Sulfuric acid (96%, 285 mL, 5.13 mol) and dichloromethane (100 mL) were mixed and the mixture was cooled with stirring to −15° C. Nitric acid (98-99%, 2.9 mL, 0.069 mol) was added to the mixture with stirring. Another portion of nitric acid (98-99%, 26.0 mL, 0.618 mol) was then added in parallel with the above obtained 1,4-butanediol monobutyrate (103 mL, 0.624 mol) at such a rate that the inner temperature was maintained below −5° C. which took 90 min. An inner temperature of +5° C. must not be exceeded for stability reasons. Directly after the addition was finished the entire crude mixture was poured into a mixture of ice and water (2.25 kg) with efficient stirring keeping the inner temperature below +5° C. Stirring was switched off and the phases were allowed to separate. The dichloromethane-layer was saved and the aqueous layer was extracted with dichloromethane (400 mL). Phase separation was followed by washing of the combined dichloromethane-layers with 8% aqueous sodium bicarbonate solution (150 mL) and water (150 mL-portions) to pH 7-8. Removal of the dichloromethane by vacuum distillation at a jacket temperature below +40° C. (important for thermal safety reasons) gave 98.5 g (73% yield) of the title compound as a pale yellow oil. The purity according to GC was 95%.

$^1$H NMR (CDCl$_3$) δ 4.50 (t, J=6 Hz, 2H), 4.13 (t, J=6 Hz, 2H), 2.30 (t, J=7.4 Hz, 2H), 1.72-1.92 (m, 4H), 1.67 (sext, J=7.4 Hz, 2H), 4.50 (t, J=7.4 Hz, 3H);
$^{13}$C NMR (CDCl$_3$) δ 173.9, 73.1, 63.6, 36.4, 25.3, 24.0, 18.8, 14.0;
IR 1732 (C=O), 1623, 1278 cm$^{-1}$.

EXAMPLE 2

Intraocular Pressure (IOP) Lowering Activity in Hypertonic Saline-Induced IOP Increase in Rabbits The Intraocular pressure (TOP) lowering activity of compound (Ia) (Example 1) was assessed in an animal model of elevated IOP.

Adults male New Zealand White rabbits weighting 1.8-2.0 Kg were used in the experiments.

IOP was measured using a Tono-Pen XL prior to hypertonic saline injection (basal) and at 30, 60, 120 and 240 min thereafter. Vehicle (5% cremophor-EL; 0.3% DMSO; 0.2 mg/ml bac in PBS pH 6.0,) or compound (Ia) dissolved in the vehicle at different concentrations (0.1%, 0.3% and 1%) was instilled as eye drops immediately after hypertonic saline injection. Eyes were randomly assigned to different treatment groups. Vehicle or compound (Ia) was directly instilled into the conjunctiva pocket at the desired doses. One drop of 0.4% oxybuprocaine hydrochloride (Novesine, Sandoz) was instilled in each eye immediately before each set of pressure measurements.

Results are reported in Table in which the ocular hypotensive activity of compound (Ia) at different is expressed as IOP change (at 60 and 120 minutes following topical administration) versus vehicle and versus IOP at basal before hypertonic saline injection.

| | IOP change | |
|---|---|---|
| Treatment | 60 min | 120 min |
| Compound (Ia) 1% | −21.1 ± 4.5 | −15.1 ± 2.3 |
| Compound (Ia) 0.3% | −16.5 ± 3.8 | −9 ± 2.1 |
| Compound (Ia) 0.1% | −10.3 ± 0.3 | −5 ± 1.8 |

The invention claimed is:

1. A compositions comprising
(A) a nitric oxide donor of formula (I) or stereoisomers thereof:

$$RC(O)O-(CH_2)_4-ONO_2 \qquad (I)$$

wherein R is a linear or branched (C$_3$-C$_5$)-alkyl chain, and
(B) an ophthalmic drug selected from one of the following groups: alpha adrenergic agonists, beta blockers, carbonic anhydrase inhibitors, prostaglandin analogs, cholinergic agonists, non-steroidal anti-inflammatory and steroidal anti-inflammatory drugs.

2. A composition according to claim 1 wherein the nitric oxide donor of formula (I) is $$CH_3(CH_2)_2C(O)O-(CH_2)_4-ONO_2 \qquad (Ia).$$

3. A composition according to claim 2 wherein the ophthalmic drug is selected from bimatoprost, latanoprost, travoprost, tafluprost, unoprostone isopropyl, apraclonidine, bromonidine, timolol, levobunolol, dorzolamide or brinzolamide.

4. A composition according to claim 1 wherein the carbonic anhydrase inhibitor is selected from dorzolamide, brinzolamide.

5. A composition according to claim 1 wherein the beta blocker selected from timolol, carteolol, betaxolol, levobunolol or metipranolol.

6. A composition according to claim 1 wherein the alpha-adrenergic agonist is selected from brimonidine, apraclonidine, epinephrine or dipivefrin.

7. A composition according to claim 1 wherein the prostaglandin analogue is selected from bimatoprost, latanoprost, travoprost, unoprostone isopropyl or tafluprost.

8. A composition according to claim 1 wherein the cholinergic agonist selected from pilocarpin, carbacol or echothiophate.

9. A composition according to claim 1 wherein the non-steroidal anti-inflammatory drug is selected from bromfenac, flurbiprofen, naproxen or ketoprofen.

10. A composition according to claim 1 wherein the steroidal anti-inflammatory drug is selected from dexamethsone, fluocinolone acetonide, triamcinolone acetonide, budesonide or prednisolone.

11. Pharmaceutical formulation comprising a composition according to claim 1 and at least an ophthalmically acceptable excipient.

12. A pharmaceutical formulation comprising a nitric oxide donor of formula (I) or stereoisomers thereof:

$$RC(O)O-(CH_2)_4-ONO_2 \qquad (I)$$

wherein R is a linear or branched (C$_3$-C$_5$)-alkyl chain, and at least an ophthalmically acceptable excipient and/or ophthalmically acceptable vehicle.

13. Pharmaceutical formulation comprising the nitric oxide donor of formula (Ia) and at least an ophthalmically acceptable excipient and/or ophthalmically acceptable vehicle.

14. A method of treating elevated intraocular pressure associated with glaucoma comprising administering to an eye of a subject in need thereof a composition according to claim 1.

15. A method of treating hypertensive glaucoma, normotensive glaucoma, secondary glaucoma, neovascular glaucoma, and/or ocular hypertension comprising administering to an eye of a subject in need thereof a composition according to claim 1.

16. A method of treating high intraocular pressure resulting from orbital edema, ischemia, intraocular inflammation, and/or pupillary block comprising administering to an eye of a subject in need thereof a composition according to claim 1.

17. A method of treating age related macular degeneration, diabetic retinopathy, retinal vein occlusion, macular degeneration, inflammatory retinal disease, and/or uveitis comprising administering to an eye of a subject in need thereof a composition according to claim 9.

18. A method of treating hypertensive glaucoma, normotensive glaucoma, secondary glaucoma, neovascular glaucoma, and/or ocular hypertension comprising administering to an eye of a subject in need thereof a nitric oxide donor of formula (Ia)

$$CH_3(CH_2)_2C(O)O-(CH_2)_4-ONO_2 \qquad (Ia).$$

19. A method of treating high intraocular pressure resulting from orbital edema, ischemia intraocular inflammation, and/or pupillary block comprising administering to an eye of a subject in need thereof a nitric oxide donor of formula (Ia)

$$CH_3(CH_2)_2C(O)O-(CH_2)_4-ONO_2 \qquad (Ia).$$

20. A method of treating age related macular degeneration, diabetic retinopathy, retinal vein occlusion, macular degeneration, inflammatory retinal disease, and/or uveitis comprising administering to an eye of a subject in need thereof a nitric oxide donor of formula (Ia)

$$CH_3(CH_2)_2C(O)O\text{—}(CH_2)_4\text{—}ONO_2 \quad \text{(Ia)}.$$

* * * * *